United States Patent
Wong et al.

(10) Patent No.: US 11,470,897 B2
(45) Date of Patent: Oct. 18, 2022

(54) SEMI TRANSPARENT NITRILE GLOVE

(71) Applicant: TOP GLOVE INTERNATIONAL SDN. BHD., Klang (MY)

(72) Inventors: Chong Ban Wong, Klang (MY); Keuw Wei Lim, Klang (MY); Kien Ben Liew, Klang (MY); Chee Kin Phang, Klang (MY)

(73) Assignee: Top Glove International SDN. BHD., Selangor (MY)

( * ) Notice: Subject to any disclaimer, the term of this patent is extended or adjusted under 35 U.S.C. 154(b) by 258 days.

(21) Appl. No.: 16/771,531

(22) PCT Filed: Dec. 19, 2018

(86) PCT No.: PCT/MY2018/050093
§ 371 (c)(1),
(2) Date: Jun. 10, 2020

(87) PCT Pub. No.: WO2019/139467
PCT Pub. Date: Jul. 18, 2019

(65) Prior Publication Data
US 2021/0169160 A1    Jun. 10, 2021

(30) Foreign Application Priority Data
Jan. 10, 2018 (MY) .......................... PI 2018700127

(51) Int. Cl.
| A41D 19/00 | (2006.01) |
| C08K 3/011 | (2018.01) |
| C08K 3/06 | (2006.01) |
| C08K 3/22 | (2006.01) |
| C08K 5/205 | (2006.01) |
| C08K 5/39 | (2006.01) |
| C08L 9/04 | (2006.01) |

(52) U.S. Cl.
CPC .......... *A41D 19/0062* (2013.01); *C08K 3/011* (2018.01); *C08K 3/06* (2013.01); *C08K 3/22* (2013.01); *C08K 5/205* (2013.01); *C08K 5/39* (2013.01); *C08L 9/04* (2013.01); *A41D 2400/52* (2013.01); *A41D 2500/50* (2013.01); *C08K 2003/2296* (2013.01); *C08K 2201/019* (2013.01)

(58) Field of Classification Search
CPC ............ A41D 19/0062; A41D 19/0055; A41D 2400/52; C08L 9/04; C08L 13/02
See application file for complete search history.

(56) References Cited

U.S. PATENT DOCUMENTS 6,566,435 B1    5/2003    Chin et al.

FOREIGN PATENT DOCUMENTS

| CN | 107216505 | 9/2017 | |
| DE | 112016005743 | 10/2018 | |
| KR | 20160140497 A | * 12/2016 | ................ C08L 9/04 |
| WO | 2017104315 | 6/2017 | |
| WO | WO-2018151393 A1 | * 8/2018 | ............. A41D 19/00 |

OTHER PUBLICATIONS

Machine translation of KR 20160140497 A (2016, 16 pages).*
Machine translation of WO-2018151393-A1 (2018, 17 pages).*

* cited by examiner

*Primary Examiner* — Brieann R Johnston
(74) *Attorney, Agent, or Firm* — Workman Nydegger

(57) ABSTRACT

A semi transparent nitrile glove comprising nitrile latex, caustic alkali, accelerators, vulcanizing agents, stabilizer and antifoaming agent, wherein the nitrile latex is any one selected from either acrylonitrile butadiene copolymer or carboxylated acrylonitrile butadiene copolymer, wherein the caustic alkali is a combination of either potassium hydroxide and ammonia or sodium hydroxide and ammonia, wherein the accelerators are chemical compounds of dithiocarbamates, wherein the vulcanizing agents are selected from both ionic and covalent vulcanizing agents, wherein the stabilizer is any one of either sodium dodecylbenzene sulfonate or sodium dodecyl sulfate and wherein the antifoaming agent is any one from a group consisting of silicone based antifoam, non-silicone based antifoam, oil based antifoam and water based antifoam wherein the semi transparent glove is without pigment and without titanium dioxide.

4 Claims, No Drawings

SEMI TRANSPARENT NITRILE GLOVE

The present application is a 371 US Nationalization of PCT Patent Application No. PCT/MY2018/050093, filed Dec. 19, 2018, which claims priority to Malaysian Patent Application No. PI 2018700127, filed Jan. 10, 2018, the disclosure of each of which is hereby incorporated by reference in its entirety.

FIELD OF THE INVENTION

The present invention relates to a composition of nitrile glove, in particular relates to a composition of semi transparent nitrile glove without pigment and/or without titanium dioxide which exhibits low percentage of opacity.

BACKGROUND OF THE INVENTION

Latex gloves have caused allergic reactions in some individuals. Hypoallergenic gloves, glove liners and powder free gloves are possible alternatives for individuals who are allergic to latex gloves. Nitrile gloves are generally made from synthetic rubber and are also an ideal alternative when natural rubber latex allergy, namely Type I is of concern. Nitrile gloves are often regarded as superior glove when it comes to puncture resistance.

Nitrile gloves are usually used to manufacture "medical grade" gloves. Nitrile gloves are preferred whenever it come into contact with aromatic petroleum and chlorinated solvents such as trichloroethylene and perchloroethylene. Nitrile gloves are resistant towards abrasions, snags and tears. Also, it is commonly used for work whereby dexterity is required. Gloves are offered in a variety of colors. Some colors are common whereas some colors are specifically chosen for certain applications or tasks.

Latex glove by nature has natural color and vinyl gloves are naturally transparent in color—common to the transparent color of shower curtains. However, nitrile gloves were introduced in a light blue color to differentiate among the latex and vinyl gloves. In current world, nitrile gloves are offered in a large variety of colors. Color doesn't affect usefulness of glove. Japanese Patent Application No.: JP 2015028224 A discloses a transparent rubber glove and method of preparing the same. U.S. Pat. No. 3,014,883 relates to transparent rubber compositions and method of manufacturing the same.

However, composition taught/disclosed in the above identified patent applications has their own disadvantages. As such, there is a need for a latex composition to prepare semi transparent glove using a more competent and cost-effective components and/or formulation, which is to overcome the above mentioned shortcomings in the prior art such as being transparent, yet producing enhanced tactile sensitivity towards objects.

SUMMARY OF THE INVENTION

A semi transparent nitrile glove comprising nitrile latex, caustic alkali, accelerators, vulcanizing agents, stabilizer and antifoaming agent, wherein the nitrile latex is any one selected from either acrylonitrile butadiene copolymer or carboxylated acrylonitrile butadiene copolymer, wherein the caustic alkali is a combination of either potassium hydroxide and ammonia or sodium hydroxide and ammonia, wherein the accelerators are chemical compounds of dithiocarbamates, wherein the vulcanizing agents are selected from both ionic and covalent vulcanizing agents, wherein the stabilizer is any one of either sodium dodecylbenzene sulfonate or sodium dodecyl sulfate and wherein the antifoaming agent is any one from a group consisting of silicone based antifoam, non-silicone based antifoam, oil based antifoam and water based antifoam wherein the semi transparent glove is without pigment and without titanium dioxide, wherein the acrylonitrile butadiene copolymer is an admixture of 25 to 35% by weight of acrylonitrile and 65 to 75% by weight of butadiene, wherein the carboxylated acrylonitrile butadiene copolymer is an admixture of 4 to 8% by weight of carboxylic acid, 25 to 35% by weight of acrylonitrile and 65 to 75% by weight of butadiene, wherein the accelerators are used in an amount ranging between 0.1 to 3.0 parts per 100 parts of the nitrile latex, wherein both the ionic vulcanizing agent and the covalent vulcanizing agent, each is used in an amount ranging between 0.1 to 3.0 parts per 100 parts of the nitrile latex, wherein the potassium hydroxide, sodium hydroxide and ammonia, each is used in an amount ranging between 0.1 to 3.0 parts per 100 parts of the nitrile latex, wherein the stabilizer is used in an amount ranging between 0.1 to 2.0 parts per 100 parts of the nitrile latex, wherein the antifoaming agent is used in an amount ranging between 0.01 to 0.10 parts per 100 parts of the nitrile latex and wherein the semi transparent glove having a mean maximum pull force of 0.51 kgf and a mean maximum catch force of 0.68 kgf.

Additional aspects, features and advantages of the invention will become apparent to those skilled in the art upon consideration of the following detailed description of preferred embodiments of the invention listed below.

DETAILED DESCRIPTION OF THE INVENTION

Detailed description of preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claim and for teaching one skilled in the art of the invention. The numerical data or ranges used in the specification are not to be construed as limiting.

The present invention relates to a composition of nitrile glove. Particularly, the nitrile glove is prepared without titanium dioxide ($TiO_2$) and without pigment to yield semi transparent nitrile glove, whereby the nitrile glove of the present invention has low percentage of opacity that is about 23%. The lower the percentage of opacity of a glove, the more transparent the glove is. The semi transparent nitrile glove includes of:
  a) nitrile latex;
  b) caustic alkali;
  c) accelerators;
  d) vulcanizing agents;
  e) stabilizer; and
  f) antifoaming agent.

The semi transparent nitrile glove of the present invention is produced without titanium dioxide ($TiO_2$) and without pigment. Commonly used pigments in glove industries are any pigment known from one skilled in the art, wherein the pigment is from any color-based organic and/or inorganic pigments such as but not limited to blue pigment and black pigment. The nitrile latex is any one selected from either acrylonitrile butadiene copolymer or carboxylated acrylonitrile butadiene copolymer, preferably carboxylated acrylonitrile butadiene copolymer.

The acrylonitrile butadiene copolymer is an admixture of 25 to 35% by weight of acrylonitrile and 65 to 75% by weight of butadiene. Whereas, the carboxylated acrylonitrile butadiene copolymer is an admixture of 4 to 8% by weight of carboxylic acid, 25 to 35% by weight of acrylonitrile and 65 to 75% by weight of butadiene. Semi transparent glove may be prepared using any other synthetic latex such as but not limited to polyisoprene, polychloroprene, polyurethane and thermoplastic elastomer in place of nitrile latex in combination with the above identified components.

The nitrile latex may be obtained from any commercially available nitrile latex suppliers. The nitrile latex is used as 100% by weight (also referred to as parts per hundred of the nitrile latex, phr), wherein the parts per hundred of the nitrile latex is used as a basis for amounting other components. The caustic alkali is a combination of either potassium hydroxide and ammonia or sodium hydroxide and ammonia, preferably a combination of potassium hydroxide and ammonia. The caustic alkali acts as pH adjuster to regulate pH value to be in a range between 9.0 to 10.5.

The potassium hydroxide, sodium hydroxide and ammonia may be obtained from any commercially available potassium hydroxide, sodium hydroxide and ammonia suppliers, respectively. The potassium hydroxide is used in an amount ranging from 0.1 to 3.0, preferably 1.7 parts per 100 parts of the nitrile latex. The sodium hydroxide is used in an amount ranging from 0.1 to 3.0, preferably 1.7 parts per 100 parts of the nitrile latex. The ammonia is used in an amount ranging from 0.1 to 3.0, preferably 0.3 parts per 100 parts of the nitrile latex.

The accelerators used in the present invention may be selected from chemical compounds of dithiocarbamates, thiuram, thiozoles, diisopropyl xanthogen and polysulphide, preferably chemical compounds of dithiocarbamates. The dithiocarbamates are selected from a group consisting of zinc diethyldithiocarbamate (ZDEC), zinc dibutyldithiocarbamate (ZDBC) and mixtures thereof, preferably mixtures thereof.

The mixture of zinc diethyldithiocarbamate (ZDEC) and zinc dibutyldithiocarbamate (ZDBC) is mixed in sufficient ratio and quantity to accelerate vulcanization. The mixture of zinc diethyldithiocarbamate (ZDEC) and zinc dibutyldithiocarbamate (ZDBC) used in an amount ranging from 0.1 to 3.0, preferably 0.75 parts per 100 parts of the nitrile latex. The dithiocarbamates may be obtained from any commercially available dithiocarbamates suppliers.

The vulcanizing agents are selected from both ionic and covalent vulcanizing agents. The ionic vulcanizing agent used in the present invention is selected from any bivalent metal oxide, preferably zinc oxide. The ionic vulcanizing agent is used in an amount ranging from 0.1 to 3.0, preferably 1.80 parts per 100 parts of the nitrile latex. The covalent vulcanizing agent used in the present invention is sulphur. The covalent vulcanizing agent is used in an amount ranging from 0.1 to 3.0, preferably 1.40 parts per 100 parts of the nitrile latex.

The ionic and covalent vulcanizing agents may be obtained from any commercially available ionic and covalent vulcanizing agent suppliers. The stabilizer used in the present invention is any one of either sodium dodecylbenzene sulfonate or sodium dodecyl sulfate. The stabilizer is used in an amount ranging from 0.1 to 2.0, preferably 0.75 parts per 100 parts of the nitrile latex. The stabilizer may be obtained from any commercially available stabilizer suppliers.

Lastly, the antifoaming agent used in the present invention is any one from a group consisting of silicone based antifoam (in emulsion form), non-silicone based antifoam, oil based antifoam and water based antifoam, preferably silicone based antifoam (in emulsion form). The antifoaming agent is used in an amount ranging from 0.01 to 0.1, preferably 0.06 parts per 100 parts of the nitrile latex. The antifoaming agent may be obtained from any commercially available antifoaming agent suppliers.

Method of manufacturing the semi transparent nitrile glove as disclosed above is by adopting a method commonly known in the glove manufacturing industry. The method of manufacturing the semi transparent nitrile glove comprises the steps of:
a) cleaning/washing formers with acid and alkaline solutions;
b) dipping the former in a coagulant solution to form coagulant coated former, wherein the coagulant solution comprises of calcium nitrate, surfactant and anti-tacking agent;
c) drying the coagulant coated former obtained in step (b) for a duration of at least 30 seconds in an oven at a temperature ranging between 100 to 180° C.;
d) dipping the coagulant coated former obtained in step (c) into a first latex formulation and thereafter subjecting the former for drying for a duration of at least 25 seconds in an oven at a temperature ranging between 50 to 100° C. to form a first layer on the coagulant coated former, wherein the first latex formulation includes components as disclosed above;
e) dipping the first layer coated former obtained in step (d) into a second latex formulation and thereafter subjecting the former for drying for a duration of at least 25 seconds in an oven at a temperature ranging between 50 to 100° C. to form a second layer on top of the first layer, wherein the second latex formulation is the same as the first latex formulation;
f) pre-leaching the second layer coated on the former with water in a temperature of about 70° C. and subjecting the former for beading and thereafter drying for a duration of at least 15 seconds in an oven at a temperature ranging between 40 to 70° C. and subsequently cooling for a duration of at least 10 seconds in a cooling tank to be at a temperature ranging between 25 to 40° C.;
g) chlorinating the pre-leached second layer coated on the former for donning purposes to produce donned layer;
h) subjecting the donned layer coated on the former to soak rinsing for a duration of at least 15 seconds at a temperature ranging between 40 to 70° C. and drying for a duration of at least 15 minutes in an oven at a temperature ranging between 100 to 150° C. to produce glove, wherein the soak rinsing is carried out to leach out chlorine residues and excess chemicals from the donned layer and wherein the glove is semi transparent nitrile glove;
i) stripping the glove obtained in step (h) and directed for stacking The semi transparent nitrile glove prepared has thickness ranging between 0.050 mm to 0.055 mm, tensile strength ranging between 22 MPa to 32.5 MPa, modulus at 500% ranging between 13.5 MPa to 25 MPa and an elongation at break ranging between 481% to 630%. The properties mentioned above are determined before and after aging and the properties are as per ASTM glove standard. The following example is constructed to illustrate the present invention in a non-limiting sense.

Example 1

Table 1 shows composition to produce the semi transparent nitrile glove.

TABLE 1

Composition of the semi transparent nitrile glove

| Chemicals | Parts per hundred rubber (phr) |
|---|---|
| Nitrile latex | 100.0 |
| Potassium hydroxide | 1.7 |
| Ammonia | 0.3 |
| Stabilizer | 0.75 |
| Accelerators | 0.75 |
| Sulphur | 1.4 |
| Zinc oxide | 1.8 |
| Antifoaming agent | 0.06 |

Example 2

Manufacturing the semi transparent nitrile glove using composition as disclosed in example 1 adopting method commonly known in the glove manufacturing industry (as discussed above). Mechanical properties (i.e. tensile strength, modulus at 500% and elongation at break) of the prepared semi transparent nitrile glove are tested according to standard ASTM testing method.

Tables 2 and 3 show the mechanical properties of the semi transparent nitrile glove prepared before and after aging. Aging treatment of the semi transparent nitrile glove may be carried out in one of the two following conditions:

i. heating at a temperature of 100° C. for a duration of about 22 hours; or
i. heating at a temperature of 70° C. for a duration of about 168 hours

TABLE 2

Mechanical properties of the semi transparent nitrile glove before aging treatment

| | Before Aging | | | |
|---|---|---|---|---|
| | Thickness, mm | Tensile strength, MPa | Elongation at break, % | Modulus at 500%, MPa |
| Minimum | 0.050 | 22.94 | 531.2 | 13.86 |
| Maximum | 0.055 | 30.90 | 629.5 | 19.43 |
| Average | 0.053 | 27.26 | 568.0 | 16.14 |
| Standard | Min 0.05 | Min 14.00 | Min 500% | N/A |

TABLE 3

Mechanical properties of the semi transparent nitrile glove after aging treatment

| | After Aging | | | |
|---|---|---|---|---|
| | Thickness, mm | Tensile strength, MPa | Elongation at break, % | Modulus at 500%, MPa |
| Minimum | 0.050 | 22.44 | 481.6 | 13.86 |
| Maximum | 0.054 | 32.30 | 563.3 | 24.78 |
| Average | 0.051 | 26.45 | 535.0 | 18.84 |
| Standard | Min 0.05 | Min 14.00 | Min 400% | N/A |

Opacity is a measure of impenetrability to electromagnetic or visible lights. Lower the opacity, more transparent a material appears. Opacity is determined by using colour spectrophotometer, which is tested according to standard ASTM testing method i.e. ASTM D2805 and ASTM D344. The opacity is measured based on following formula:

$$\text{Opacity}(\%) = \frac{Y_{BLACK}}{Y_{WHITE}} \times 100\%$$

Remark:
Y is tristimulus value in the Commission Internationale de l'éclairage (CIE) system. 100% opacity is considered as complete hiding whereby there is no differences observed between the drawdown over black and white.

Table 4 shows result of colour space testing performed on the semi transparent nitrile glove of the present invention and prior arts.

TABLE 4

Opacity of the semi transparent nitrile glove of the present invention and prior arts

| Colour space | Glove of the present invention | Vinyl glove | Cast Polyethylene (CPE) glove | Thermoplastic Elastomer (TPE) glove | Normal nitrile white glove |
|---|---|---|---|---|---|
| L | 93.65 | 93.20 | 93.76 | 94.05 | 94.47 |
| a | −0.70 | −0.49 | −0.26 | −0.31 | −0.49 |
| b | 4.76 | 5.27 | 3.56 | 3.91 | 3.68 |
| Opacity, % | 22.91 | 22.23 | 16.81 | 17.44 | 68.94 |

Remark:
L for lightness
a and b for colour components green-red and blue-yellow
The lightness, L represents darkest black at L=0 and the brightest white at L=100
The colour channels, a and b represent true neutral grey values at a=0 and b=0

Sensitivity of touch and/or holding for gloves is desirable at all items especially when handling small objects and holding delicate items. Sensitivity is related to (1) catch force directed into grasp surface relative to load force applied along the surface and also to (2) friction between hand and objects. A high sensitivity glove may require lower catch force to maintain same safety margin against an object in the hand slipping under load.

It reduces tendency for torques to be generated and hence allows user to catch using a lower grip force. Thin and low weight semi transparent nitrile glove of the present invention provides a high sensitivity glove that enables users grasp objects with lower catch force. Table 5 shows results of sensitivity of touch in terms of pull force (kgf) and catch force (kgf) of the semi transparent nitrile glove of the present invention and prior arts.

TABLE 5

Maximum pull force (MPF) and maximum catch force (MCF) of the semi transparent nitrile glove of the present invention and prior arts

| | Glove of the present invention | | Normal nitrile rubber (NBR) Glove | | Higher weight nitrile rubber (NBR) Glove | |
|---|---|---|---|---|---|---|
| Repetition no. | MPF (kgf) | MCF (kgf) | MPF (kgf) | MCF (kgf) | MPF (kgf) | MCF (kgf) |
| 1. | 0.78 | 0.74 | 0.58 | 1.39 | 1.65 | 4.96 |
| 2. | 0.49 | 0.79 | 0.87 | 1.28 | 1.22 | 3.63 |
| 3. | 0.40 | 0.87 | 0.49 | 1.11 | 1.20 | 3.56 |
| 4. | 0.31 | 0.64 | 0.74 | 1.61 | 1.49 | 3.09 |
| 5. | 0.63 | 0.78 | 0.83 | 1.58 | 1.59 | 3.95 |
| 6. | 0.36 | 0.45 | 0.60 | 1.74 | 1.29 | 4.80 |

TABLE 5-continued

Maximum pull force (MPF) and maximum catch force (MCF) of the semi transparent nitrile glove of the present invention and prior arts

| | Glove of the present invention | | Normal nitrile rubber (NBR) Glove | | Higher weight nitrile rubber (NBR) Glove | |
|---|---|---|---|---|---|---|
| Repetition no. | MPF (kgf) | MCF (kgf) | MPF (kgf) | MCF (kgf) | MPF (kgf) | MCF (kgf) |
| 7. | 0.51 | 0.66 | 0.94 | 1.45 | 1.38 | 3.50 |
| 8. | 0.50 | 0.68 | 1.21 | 1.36 | 1.04 | 3.55 |
| 9. | 0.46 | 0.60 | 0.58 | 1.49 | 0.54 | 3.48 |
| 10. | 0.65 | 0.56 | 1.02 | 1.41 | 0.43 | 3.18 |
| Mean | 0.51 | 0.68 | 0.79 | 1.44 | 1.18 | 3.77 |

Remark:
1. Characteristics of the semi transparent nitrile glove of the present invention:
   Mass: 2.7 g
   Cuff thickness: 0.047 mm
   Palm thickness: 0.055 mm
   Fingertip thickness: 0.089 mm
2. Characteristics of the normal NBR glove:
   Mass: 5.0 g
   Cuff thickness: 0.073 mm
   Palm thickness: 0.106 mm
   Fingertip thickness: 0.125 mm
3. Characteristics of the higher weight NBR glove:
   Mass: 16.0 g
   Cuff thickness: 0.192 mm
   Palm thickness: 0.251 mm
   Fingertip thickness: 0.355 mm Based on the results above, it is apparent that the semi transparent nitrile glove of the present invention complies with the ASTM standard requirements set in context of the mechanical properties such as tensile strength, modulus at 500% and elongation at break. The semi transparent nitrile glove of the present invention shows apparent transparency (with opacity 22.91%) in comparison with the other types of gloves available in the market. Also, the semi transparent nitrile glove of the present invention shows higher sensitivity of touch (with mean MPF and mean MCF of 0.51 kgf and 0.68 kgf, respectively) in comparison with other NBR gloves available in the market.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including" and "having" are inclusive and therefore specify the presence of stated features, integers, steps, operations, elements and/or components, but do not preclude the presence or addition of one or more other features, integers, steps, operations, elements, components and/or groups thereof.

The method steps, processes and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

The invention claimed is:

1. A semi-transparent nitrile glove, without pigment and/or without titanium dioxide, comprising:
   nitrile latex, wherein the nitrile latex is either acrylonitrile butadiene copolymer or carboxylated acrylonitrile butadiene copolymer, wherein the acrylonitrile butadiene copolymer is an admixture of 25% to 35% by weight of acrylonitrile and 65% to 75% by weight of butadiene and wherein the carboxylated acrylonitrile butadiene copolymer is an admixture of 4% to 8% by weight of carboxylic acid, 25% to 35% by weight of acrylonitrile and 65 to 75% by weight of butadiene;
   0.1 to 3.0 parts per 100 parts of the nitrile latex of caustic alkali, wherein the caustic alkali is selected from a combination of either potassium hydroxide and ammonia or sodium hydroxide and ammonia;
   0.1 to 3.0 parts per 100 parts of the nitrile latex of accelerators, wherein the accelerators are chemical compounds of dithiocarbamates;
   0.1 to 3.0 parts per 100 parts of the nitrile latex of vulcanizing agents, wherein the vulcanizing agents are selected from a combination of both ionic and covalent vulcanizing agents;
   0.1 to 2.0 parts per 100 parts of the nitrile latex of stabilizer, wherein the stabilizer is any one of either sodium dodecylbenzene sulfonate or sodium dodecyl sulfate; and
   0.01 to 0.10 parts per 100 parts of the nitrile latex of antifoaming agent, wherein the antifoaming agent is selected from the group consisting of silicone based antifoam, non-silicone based antifoam, oil based antifoam and water based antifoam.

2. The semi-transparent nitrile glove as claimed in claim 1 wherein the accelerators are a mixture of zinc diethyldithiocarbamate (ZDEC) and zinc dibutyldithiocarbamate (ZDBC).

3. The semi-transparent nitrile glove as claimed in claim 1 wherein the ionic vulcanizing agent is zinc oxide.

4. The semi-transparent nitrile glove as claimed in claim 1 wherein the covalent vulcanizing agent is sulphur.

* * * * *